(12) United States Patent
Koo et al.

(10) Patent No.: US 8,445,409 B2
(45) Date of Patent: May 21, 2013

(54) USE OF 5-BENZYLOXYMETHYL-1,2-ISOXAZOLINE DERIVATIVES AS A HERBICIDE

(75) Inventors: Suk-Jin Koo, Daejeon (KR); Ki-Hwan Hwang, Daejeon (KR)

(73) Assignee: Moghu Research Center Ltd., Daejeon (KR)

( * ) Notice: Subject to any disclaimer, the term of this patent is extended or adjusted under 35 U.S.C. 154(b) by 29 days.

(21) Appl. No.: 13/168,452

(22) Filed: Jun. 24, 2011

(65) Prior Publication Data

US 2011/0306496 A1    Dec. 15, 2011

Related U.S. Application Data

(63) Continuation-in-part of application No. 12/122,312, filed on May 16, 2008, now Pat. No. 7,998,902.

(30) Foreign Application Priority Data

Jun. 22, 2007   (KR) .................. 10-2007-0061711

(51) Int. Cl.
*A01N 43/74*   (2006.01)
*A01N 43/80*   (2006.01)

(52) U.S. Cl.
USPC .......................................... 504/271; 504/100

(58) Field of Classification Search
USPC ................................................ 504/271, 100
See application file for complete search history.

(56) References Cited

U.S. PATENT DOCUMENTS

| | | | |
|---|---|---|---|
| 4,060,402 A | | 11/1977 | Tomita et al. |
| 4,983,210 A | * | 1/1991 | Rheinheimer et al. ........ 504/248 |
| 6,838,416 B2 | * | 1/2005 | Ryu et al. ..................... 504/271 |

OTHER PUBLICATIONS

Yelverton (A new herbicide for weeds in bermudagrass and zoysiagrass, May 2003).*

* cited by examiner

*Primary Examiner* — Fereydoun G Sajjadi
*Assistant Examiner* — Danielle Sullivan
(74) *Attorney, Agent, or Firm* — The PL Law Group, PLLC

(57) ABSTRACT

A method of selectively controlling annual bluegrass and/or goosegrass in turf grass, the method includes applying 5-benzyloxymethyl-1,2-isoxazoline derivative compounds, pre-emergence or post-emergence, to goosegrass and/or annual bluegrass in turf grass.

20 Claims, 8 Drawing Sheets

USE OF 5-BENZYLOXYMETHYL-1,2-ISOXAZOLINE DERIVATIVES AS A HERBICIDE

CROSS-REFERENCE TO RELATED APPLICATIONS AND CLAIM OF PRIORITY

This application is a Continuation-in-part of Applicant's Ser. No. 12/122,312 filed in the U.S. Patent & Trademark Office on 16 May 2008 and assigned to the assignee of the present invention, the disclosure of which is incorporated herein in its entirety by reference, and which claims the benefit of Korean Patent Application No. 10-2007-0061711, filed on 22 Jun. 2007, in the Korean Intellectual Property Office, the disclosure of which is incorporated herein in its entirety by reference.

BACKGROUND OF THE INVENTION

1. Field of the Invention

The present invention relates to a method of selectively controlling annual bluegrass and/or goosegrass in turfgrass.

2. Description of the Related Art

Korean Patent Registration No. 10-0392072 discloses a rice paddy herbicide which includes as an active ingredient 5-benzyloxymethyl-1,2-isoxazoline derivative compounds of following formula (I):

(I)

wherein, $X_1$, $X_2$ and $X_3$ are each a hydrogen, a methyl group, a halogen group, a methoxy group or a nitro group (provided that all of $X_1$, $X_2$ and $X_3$ cannot be a hydrogen at the same time); and $Y_1$, $Y_2$ and $Y_3$ are each a hydrogen or a fluorine.

It has been already indicated in U.S. Pat. No. 4,983,210 and Japanese Patent No. 09,143,171 that the above-described 5-benzyloxymethyl-1,2-isoxazoline derivative compound as a paddy field herbicide is better than the isoxazoline derivatives of prior art in terms of safety of rice crops and when applied to soil it has herbicidal activity of controlling various types of weeds that are found in a rice paddy field such as barnyardgrass, *Scirpus juncoides* Roxb., *Monochoria vaginalis* Presl., *Cyperus serotinus* Rottb., and *Sagittaria pigmaea* Miq., etc.

However, other than as a herbicide for rice paddy field, there has been no other uses described in said documents for 5-benzyloxymethyl-1,2-isoxazoline derivative compound of the above-stated general formula (I).

There are two main types of herbicide being used, i.e., one for paddy field and the other for upland field. Depending on the place it is applied, the method and rate of a herbicide may vary.

The inventors of the present invention found that 5-benzyloxymethyl-1,2-isoxazoline derivative compounds, which had been reported to be a good herbicide for transplanted paddy rice, also had an excellent crop safety for upland crops, turfgrasses, and direct-seeded rice and controlled various important grass weeds; therefore, the said compound(s) are excellent selective herbicide(s) for upland crops, turfgrasses, and direct-seeded rice. As a result, the present invention has been completed.

SUMMARY OF THE INVENTION

According to an aspect of the present invention, a method of selectively controlling annual bluegrass and/or goosegrass in the presence of turf grass, the method including: obtaining 5-benzyloxymethyl-1,2-isoxazoline derivative compounds of the following formula (I) as an active ingredient:

(I)

wherein, $X_1$, $X_2$ and $X_3$ are each a hydrogen, a methyl group, a halogen group, a methoxy group or a intro group, provided that all of $X_1$, $X_2$ and $X_3$ cannot be a hydrogen at the same time; and $Y_1$, $Y_2$ and $Y_3$ are each a hydrogen or a fluorine; and applying said derivative compounds, pre-emergence or post-emergence, to goosegrass or annual bluegrass in turf grass.

The said 5-benzyloxymethyl-1,2-isoxazoline derivative compound may be 5-(2,6-difluorobenzyl)oxymethyl-5-methyl-3-(4-methylthiophen-5-yl)-1,2-isoxazoline compound of the following formula (II):

(II)

The turf grass may include at least one of zoysiagrass, bentgrass, Kentucky bluegrass, Perennial ryegrass and a combination thereof.

The derivative compounds may be applied at pre-emergence or post-emergence, to annual bluegrass or goosegrass in turf grass.

According to an aspect of the present invention, a method of selectively controlling annual bluegrass and/or goosegrass in turf grass while leaving the turf grass substantially unharmed, the method including: obtaining 5-benzyloxymethyl-1,2-isoxazoline derivative compounds of the formula (I) as an active ingredient.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein:

FIG. 1 shows the herbicidal activity of the test substance of the present invention when it was applied as pre-emergence treatment in an upland condition. The photo on the left is for the crops; specifically, from the left side of the pot, there are corn (ZEAMX), soybean (GLYMX), cotton (GOSHI), wheat (TRIAZ) and rice (ORYSA). The left pot is the control group to which the test substance was not applied and the right pot is the one after application with the test substance at a dosage of 500 g/ha. The photo on the right is for the weeds; specifically, the upper left pot is the control group without any treatment, and others are after application with the test substance at a dosage of 125, 250, or 500 g/ha, clockwise starting from the control. Inside each pot, broadleaf weeds such as common cocklebur (XANST), Indian joint-vetch (AESIN), velvetleaf (ABUTH), morningglory (IPOSP) were planted in the top part of the pot while in the bottom part the gramineous weeds such as barnyardgrass (ECHCG), large crabgrass (DIGSA), green foxtail (SETVI), fall panicum (PANDI) were planted. As seen from the photo, the test substance showed a remarkable effect of controlling all of the gramineous weeds at a dosage of 125 g/ha or more, while it had almost no effect to the broadleaf weeds.

FIG. 2 shows the herbicidal activity of the test substance of the present invention when it was applied as post-emergence treatment in an upland condition. Especially, the test substance was applied to the crops and the weeds after they have already grown to a certain growth stage (i.e., three-leaf stage). The photo on the left is for the crops wherein the left pot is a control group while the right pot is for the treatment with the test substance at a dosage of 500 g/ha. The photo on the right is for the weeds, indicating that the gramineous weeds were well controlled while the broad-leaf weeds were somewhat controlled showing a mild suppression effect.

FIG. 3 shows a safety test result of the test substance of the present invention to turf species. Specifically, the photo on the left is bentgrass and one on the right is cool season turfgrass including Kentucky bluegrass and perennial ryegrass. "Mat" indicates that a transplanted commercial sod used for an experiment while "Seedling" indicates that the turf grass was grown by direct seeding. In each photo, the one at the far left side corresponds to a control group while the remaining indicates the treatment with the test substance at a dosage described therein. There was no phytotoxicity for bentgrass both in "Mat" and "Seedling" group at a dosage as high as 4,000 g/ha. It was also safe to Kentucky bluegrass and perennial ryegrass.

FIG. 4 shows a result of comparative experiment between the test substance of the present invention and a commercial herbicide, Dithiopyr, tested for Kentucky bluegrass. Pots in the top panel correspond to the Dithiopyr-treated group [1,920 (4× standard rate), 960 (2× standard rate), 480 (standard rate) g ai/ha] and the control group while the bottom panel corresponds to the test substance-treated group [4000 g, 2000 g, 1000 g ai/ha] and the untreated control group, respectively. Dithiopyr somewhat suppressed the growth of turfgrass even at a standard rate, and phytotoxicity was more evident for two or four times of the standard rate (i.e., 2× and 4×). On the other hand, the test substance showed no phytotoxicity at all at a dosage as high as 4,000 g/ha.

DETAILED DESCRIPTION OF THE INVENTION

The selective control of unwanted vegetation, such as, for example, weeds, is a major industry. Vegetation can be controlled using herbicides that are non-selective or selective, and systemic or contact. Non-selective herbicides kill or damage all plants to which they are applied, i.e., both desired and undesired vegetation. In contrast, selective herbicides eliminate or inhibit the growth of unwanted vegetation, while leaving the desired vegetation relatively unharmed. The term "selective herbicide" is a well known term so that one of ordinary skill in the art would know what was meant by "selective herbicide" as evidenced by U.S. Pat. No. 6,972,273. Likewise, "selectively controlling A in the presence of B" or "selectively controlling in B" means that the growth of A is eliminated or inhibited, while leaving B relatively unharmed. One of ordinary skill in the art would know what was meant by "selective controlling A in the presence of B".

In order to achieve the above-stated object, the present invention provides 5-benzyloxymethyl-1,2-isoxazoline derivative compounds of the following general formula (I) as an upland herbicide, a turf herbicide or a herbicide for direct-seeded paddy field rice:

(I)

wherein, $X_1$, $X_2$ and $X_3$ are each a hydrogen, a methyl group, a halogen group, a methoxy group or a nitro group (provided that all of $X_1$, $X_2$ and $X_3$ cannot be a hydrogen at the same time); and $Y_1$, $Y_2$ and $Y_3$ are each a hydrogen or a fluorine.

Furthermore, the present invention provides 5-(2,6-difluorobenzyl) oxymethyl-5-methyl-3-(4-methylthiophen-5-yl)-1,2-isoxazoline compound (herein after referred to as "test substance") of the following formula (II), which is included in the above general formula (I) and has an activity as a field herbicide, a turf herbicide or a herbicide for direct-seeded paddy field rice:

(II)

Furthermore, the present invention provides a field herbicide, a turf herbicide or a herbicide for direct-seeded paddy field rice which includes the compound of general formula (I) or formula (II) as an active ingredient and a solid carrier, a liquid carrier or a surfactant.

The solid carriers which can be included in the herbicide of the present invention includes the following: inorganic powder such as kaolin, bentonite, montmorilonite, talc, diatomite, mica, gypsum, calcium carbonate, apatite and silicon hydroxide; plant powder such as soybean flour, wheat flour, saw dust, tobacco powder, starch powder and crystalline cellulose; polymeric material such as petroleum resin, vinyl chloride resin and ketone resin; alumina; and wax. The liquid carriers which can be included in the herbicide of the present invention includes the following: alcohols such as methanol, ethanol, ethylene glycol and benzyl alcohol; aromatic hydrocarbons such as benzene, toluene, xylene and methyl naphthalene; halogenated hydrocarbons such as chloroform, carbon tetrachloride and chlorobenzene; ethers such as dioxane and tetrahydrofuran; ketones such as acetone, methylethyl ketone and cyclohexanone; esters such as ethyl acetate, butyl acetate and ethylene glycol acetate; amides such as dimethylformamide; nitriles such as acetonitrile; ether alcohols such as ethyl glycol and ethyl ether; and water. The surfactants which can be included in the herbicide of the present invention includes the following: cationic surfactants such as bromocetyltrimethyl ammonium salt; anionic surfactants such as alkyl aryl sulfonic acid, alkyloxy sulfonic acid, aryl sulfonic acid, alkaline metal salts, alkaline earth metal salts and ammonium salts thereof; and non-ionic surfactants such as aliphatic alcohols, castor oil, a condensate between naphthalene or naphthalene sulfonate and phenol or formaldehyde.

In a single active ingredient formulation as an upland herbicide, a turf herbicide or a herbicide for direct-seeded rice, the compound of general formula (I) or formula (II) is included in an amount of 1 to 80% by weight (w/w) based on the total weight of the final product. In addition, as an active ingredient in a mixture with one or more other active ingredients, it is preferably included in an amount of 1 to 40% by weight (w/w) based on the total weight of the final product.

The present invention further provides 5-(2,6-difluorobenzyl)oxymethyl-5-methyl-3-(4-methylthiophen-5-yl)-1,2-isoxazoline compound of the formula (II), which has an excellent herbicidal activity against the gramineous weeds when it is applied to a field, a turf or a direct-seeded paddy field rice.

The gramineous weed is one of the most common weeds found in crop field and non-agricultural lot. When the compound of 5-(2,6-difluorobenzyl)oxymethyl-5-methyl-3-(4-methylthiophen-5-yl)-1,2-isoxazoline was applied to several major crops including corn, soybean, wheat and cotton, etc. before or after germination, the gramineous weeds were selectively controlled. Furthermore, when warm season turfgrass such as Zoysiagrass or cool season turfgrass such as bentgrass, Kentucky bluegrass, perennial rye grass, etc. were applied with said compound before or after the germination, it was confirmed that various types of gramineous weeds including large crabgrass, annual bluegrass and goosegrass were selectively controlled. Thus, 5-benzyloxymethyl-1,2-isoxazoline derivative compound of the present invention can be used as an upland herbicide as well as a turf herbicide.

The present invention further provides a method for selective control of barnyardgrass, green foxtail, fall panicum, or large crabgrass in corn, soybean, wheat, cotton, hot pepper, Chinese cabbage, sesame, onion, garlic, tomato or potato before or after the germination with 5-benzyloxymethyl-1,2-isoxazoline derivative compound of the above-described general formula (I) or 5-(2,6-difluorobenzyl)oxymethyl-5-methyl-3-(4-methylthiophen-5-yl)-1,2-isoxazoline of the above-described formula (II).

The present invention further provides a method of selective control of goosegrass and/or annual bluegrass in warm season turfgrasses such as zoysiagrass and/or cool season turfgrasses such as bentgrass, Kentucky bluegrass, perennial ryegrass by pre-emergence or post-emergence application with 5-benzyloxymethyl-1,2-isoxazoline derivative compound of the above-described general formula (I) or 5-(2,6-difluorobenzyl)oxymethyl-5-methyl-3-(4-methylthiophen-5-yl)-1,2-isoxazoline of the above-described formula (II).

Herein below, the present invention is described in greater detail with reference to the following examples. However, they are only to exemplify the present invention and in no case it is construed that the present invention is limited thereto.

EXAMPLES

Example 1

Evaluation of Field Herbicidal Activity of 5-(2,6-difluorobenzyl)oxymethyl-5-methyl-3-(4-methylthiophen-5-yl)-1,2-isoxazoline (Herein after Referred to as "Test Substance")

The test substance used in the present invention was provided from Korean Research Institute of Chemical Technology (KRICT), the owner of Korean Patent Registration No. 0392072.

To a rectangular plastic pot having a surface area of 300 $cm^2$, mixed soils including blend bed soil (Boonong, Horticultural Bed Soil No. 3) and sandy loam soil were filled (mixing ratio, 1:1). Seeds of the eight different types of weeds including gramineous weed such as barnyardgrass, large crabgrass, green foxtail, fall panicum, and broadleaf weed such as common cocklebur, velvetleaf, Indian joint-vetch, and morningglory were sown. To the other pot containing the same soil mixture, seeds of the five different types of crops including corn, soybean, cotton, wheat and rice were sown. Pots were kept in a greenhouse of which temperature was maintained at 25~30° C. (day) or 15~25° C. (night), and regularly watered.

After fourteen days and when the crops and the weeds reached their three-leaf stage, the other set of a crop pot and a weed pot were prepared by the same method as described above. Then, "test substance" was sprayed thereto. In this case, spray treatment to the plants after they have grown for two weeks corresponded to post-emergence treatment while spray treatment to the seeds right after the sowing corresponded to pre-emergence treatment. Spray was carried out by using a track sprayer (R&D Sprayer, USA) equipped with a Teejet 8002 nozzle (Spraying Systems Co., USA). Spray volume was adjusted to 300 L/ha. The spray solution was prepared by dissolving the "test substance" in acetone and adding the same volume of 0.2% (v/v) Tween 20 aqueous solution. Dosage of the test substance was 500, 250, 125, 62.5 or 31.3 g/ha. Two weeks after the spray of the test substance, efficacy and phytotoxic effect to the crops and the weeds were visually measured based on a 0 to 10 scale (0: no efficacy, 10: completely killed). The results are summarized in the following Table 1.

Example 2

Use as a Turf Herbicide

From the results of the above Example 1, it was confirmed that the test substance of the present invention has an excellent effect of controlling gramineous weeds such as large crabgrass. Meanwhile, large crabgrass is one of the major

TABLE 1

The activity of the test substance measured in an upland condition (pot test).

| Dosage | Crops | | | | | Gramineous weed | | | | Broadleaf weed | | | |
|---|---|---|---|---|---|---|---|---|---|---|---|---|---|
| (g/ha) | Corn | Rice | Wheat | Soybean | Cotton | Barnyard-grass | Foxtail | Fall *panicum* | Large crabgrass | Cocklebur | Velvetleaf | Indian joint-vetch | Morning-glory |
| Pre-emergence treatment: Soil treatment | | | | | | | | | | | | | |
| 500 | 0 | 0 | 0 | 0 | 0 | 10 | 10 | 10 | 10 | 0 | 0 | 0 | 2 |
| 250 | 0 | 0 | 0 | 0 | 0 | 10 | 9 | 9 | 10 | 0 | 0 | 0 | 2 |
| 125 | 0 | 0 | 0 | 0 | 0 | 10 | 9 | 9 | 9 | 0 | 0 | 0 | 1 |
| 62.5 | 0 | 0 | 0 | 0 | 0 | 4 | 3 | 8 | 9 | 0 | 0 | 0 | 0 |
| 31.2 | 0 | 0 | 0 | 0 | 0 | 2 | 1 | 5 | 1 | 0 | 0 | 0 | 0 |
| Post-emergence treatment: Foliar spray at three leaf stage of the weeds | | | | | | | | | | | | | |
| 500 | 8 | 0 | 0 | 6 | 0 | 9 | 9 | 8 | 9 | 7 | 6 | 4 | 3 |
| 250 | 3 | 0 | 0 | 2 | 0 | 7 | 5 | 6 | 6 | 3 | 3 | 3 | 1 |
| 125 | 2 | 0 | 0 | 0 | 0 | 3 | 2 | 3 | 5 | 1 | 1 | 2 | 0 |
| 62.5 | 2 | 0 | 0 | 0 | 0 | 2 | 1 | 1 | 3 | 0 | 0 | 1 | 0 |
| 31.2 | 0 | 0 | 0 | 0 | 0 | 0 | 0 | 0 | 1 | 0 | 0 | 0 | 0 |

*Visual measurement: 0, no efficacy/no phytotoxic effect; 10, completely killed

Figure 1:
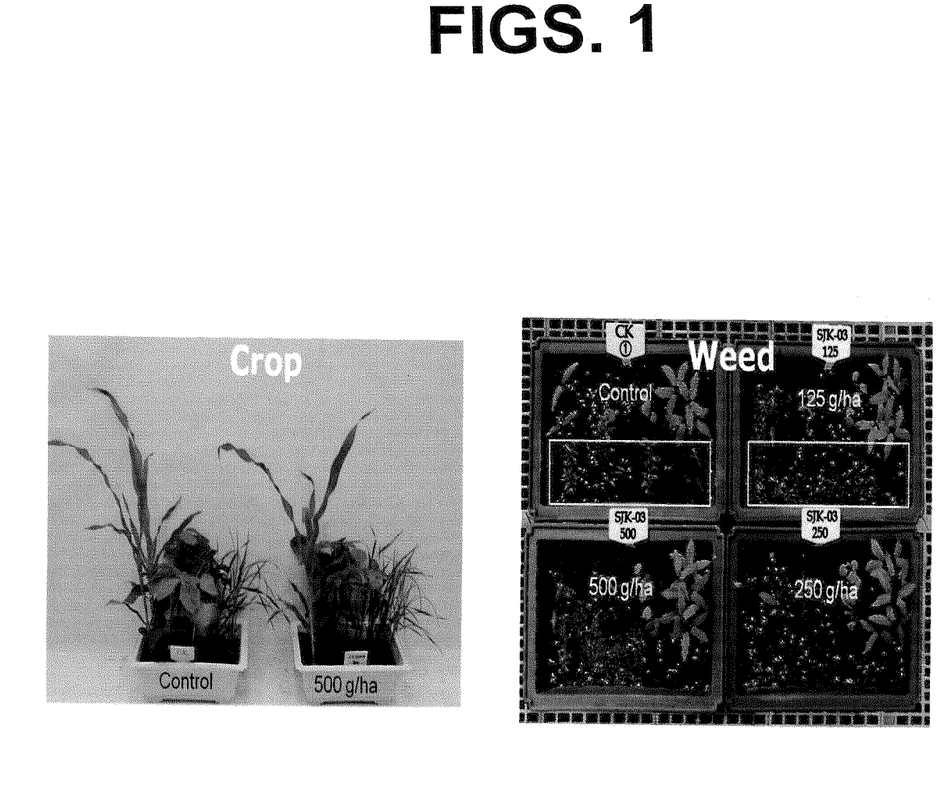
Figure 2:
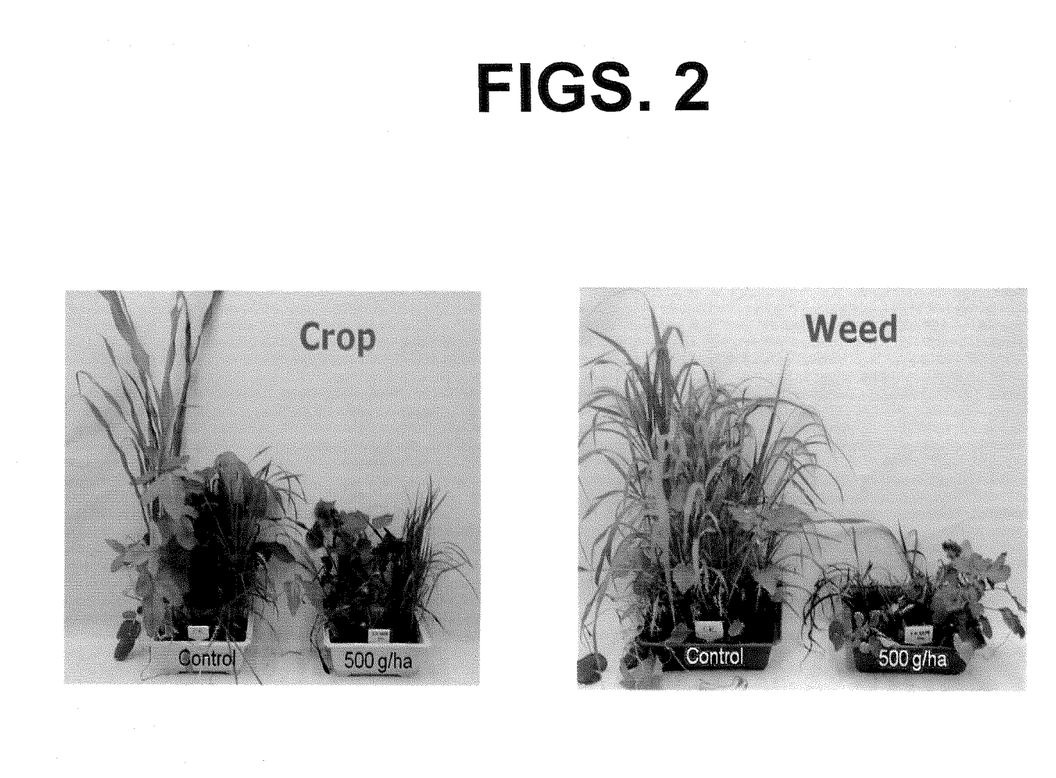
Figure 3:
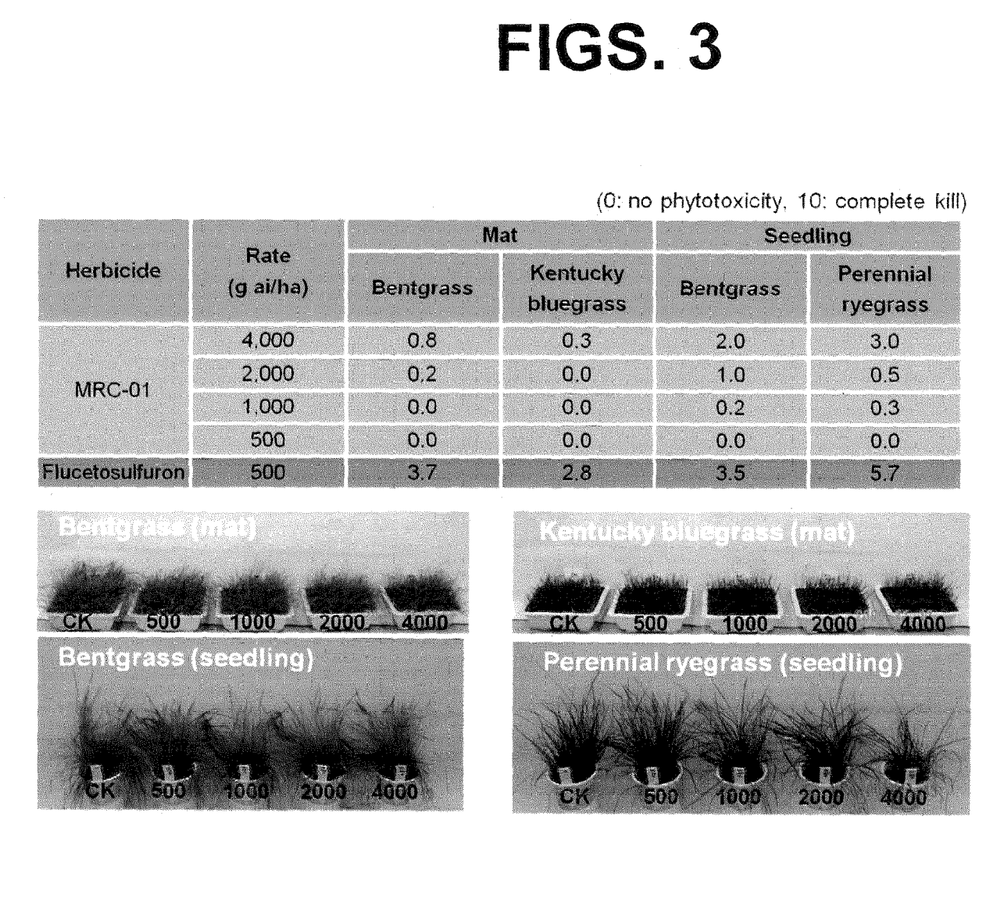

As shown in the above Table 1, when the test substance of the present invention was applied at pre-emergence timing to the crops such as corn, rice, wheat, soybean and cotton, it was completely safe without any phytotoxic effect to the crops at dosage of 500 g/ha. On the other hand, the gramineous weeds such as barnyardgrass, green foxtail, large crabgrass and fall panicum were effectively controlled at dosage of 125 g/ha or more. Broadleaf weeds were not affected (see, FIG. 1). In the case of post-emergence treatment, the test substance was not safe to corn and soybean (i.e., strong phytotoxic effect was observed). However, it was safe to rice, wheat and cotton. It was found that at the dosage of 500 g/ha most of the gramineous weeds were controlled while the herbicidal effect decreased at lower application rate (FIG. 3). In post-emergence application, broadleaf weeds in addition to grassy weeds are well controlled at 500 g/ha. According to these results, it was found that the test substance of the present invention had a higher safety and better herbicidal efficacy in pre-emergence treatment than in post-emergence treatment. In pre-emergence application, and its weed control spectrum corresponded to gramineous weeds.

Based on the above results, it is confirmed that the compound of the present invention can be used, by pre and post-emergence application, for controlling gramineous weeds in upland crops such as corn, wheat, soybean and cotton, etc. besides paddy rice. In addition, because there is no herbicidal effect to broadleaved plants by the test substance of the present invention, it its believed that the compound of the present invention can be used for selective control of gramineous weeds in fruits and vegetables such as hot pepper, Chinese cabbage, sesame, onion, garlic, tomato and potato that belong to broad-leaf plant family.

target weeds to be controlled not only for crops but also for turf (e.g., golf course and amenity area, etc.). As such, once safety is proven for turfgrass, the compound can be used as a turf herbicide. Thus, the test substance of the present invention was tested to evaluate safety to several kinds of warm and cool season turfgrasses.

Commercially available sod mats of zoysiagrass and bentgrass, Kentucky bluegrass, and perennial ryegrass were purchased. After cutting each turf sod mat in a size of 10 cm×20 cm, it was transplanted to a rectangular plastic pot having a surface area of 300 $cm^2$ wherein mixed soils including blend of a bed soil (Boonong, Horticultural Nursery Soil No. 3) and sandy loam soil were filled (mixing ratio, 1:1). After transplanting, the grass was mowed (0.5~1.0 cm in height) once a week, and kept for one month in a greenhouse maintained at 25~30° C. (day) or 15~25° C. (night), then the test substance of the present invention was applied at dosage of 4, 2, 1 and 0.5 kg/ha. As a reference, Dithiopyr (32% EC, manufactured by Dongbu Hannong Chemical Company, KOREA) was applied at the recommended rate of 0.48 kg/ha, or twice or quadruple amount thereof, i.e., 0.96 and 1.92 kg/ha, respectively. Spray was made by a track sprayer equipped with a Teejet 8002 nozzle. Spray volume was adjusted to 2,000 L/ha, which was a typical value for an Asian (Korea and Japan) golf course. The spray solution was prepared by dissolving the "test substance" in acetone and adding the same volume of 0.2% (v/v) Tween 20 aqueous solution. Two, four or six weeks after the spray of the test substance, phytotoxicity to the turfgrass were visually evaluated based on 0 to 10 scale (0: no phytotoxic effect, 10: completely killed). The test was conducted in a randomized block design with a three replicates and the results were summarized in the following Table 2 is an average value of the replicates.

TABLE 2

Safety test (i.e., phytotoxic effect measurement) for the test substance and the control herbicide *

| | | Warm season turfgrass | | | Cold season turfgrass | | | | | | | | |
| | | Zoysiagrass | | | Bentgrass | | | Kentucky bluegrass | | | Perennial ryegrass | | |
| Substance | Dosage (kg/ha) | Week 2 | Week 4 | Week 6 | Week 2 | Week 4 | Week 6 | Week 2 | Week 4 | Week 6 | Week 2 | Week 4 | Week 6 |
|---|---|---|---|---|---|---|---|---|---|---|---|---|---|
| Test substance | 4 | 2.7 | 1.7 | 1.0 | 2.3 | 3.0 | 2.0 | 2.8 | 3.0 | 1.0 | 3.0 | 2.7 | 2.0 |
| | 2 | 1.3 | 0.2 | 0.0 | 2.3 | 1.7 | 1.0 | 2.7 | 1.3 | 0.0 | 2.7 | 1.3 | 1.0 |
| | 1 | 0.7 | 0.0 | 0.0 | 1.8 | 0.5 | 0.2 | 0.8 | 0.7 | 0.0 | 0.7 | 0.3 | 0.0 |
| | 0.5 | 0.0 | 0.0 | 0.0 | 1.3 | 0.2 | 0.0 | 0.3 | 0.2 | 0.0 | 0.3 | 0.0 | 0.0 |
| | 0.25 | 0.0 | 0.0 | 0.0 | 0.8 | 0.0 | 0.0 | 0.0 | 0.0 | 0.0 | 0.0 | 0.0 | 0.0 |
| Dithiopyr | 1.92 | 3.7 | 3.3 | 3.0 | 3.3 | 4.2 | 4.2 | 3.7 | 4.2 | 4.2 | 3.3 | 2.7 | 2.3 |
| | 0.96 | 2.3 | 1.5 | 1.3 | 2.3 | 1.7 | 2.0 | 2.2 | 2.7 | 2.7 | 2.0 | 2.0 | 1.3 |
| | 0.48 | 1.0 | 1.0 | 0.7 | 1.5 | 0.3 | 0.3 | 1.5 | 0.5 | 0.7 | 1.3 | 0.3 | 0.3 |

* Visual assessment: 0, no phytotoxic effect; 10, completely killed

Figure 4:
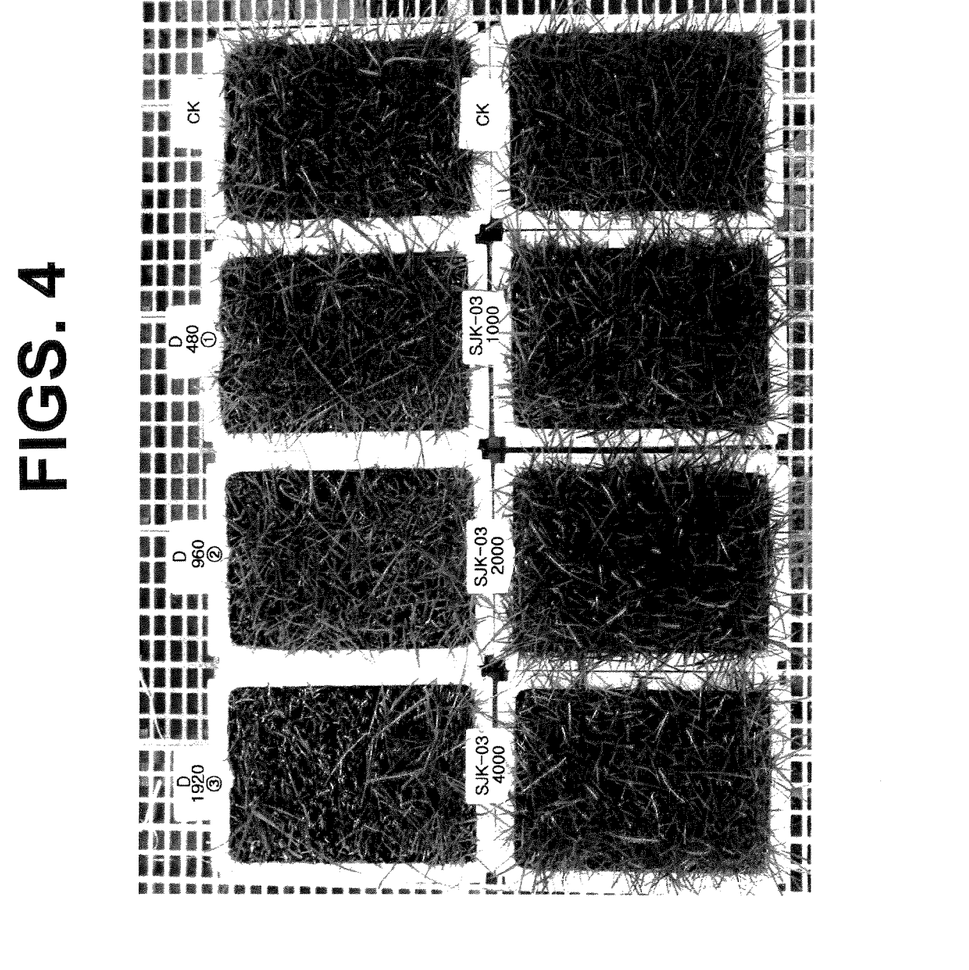
Figure 5:
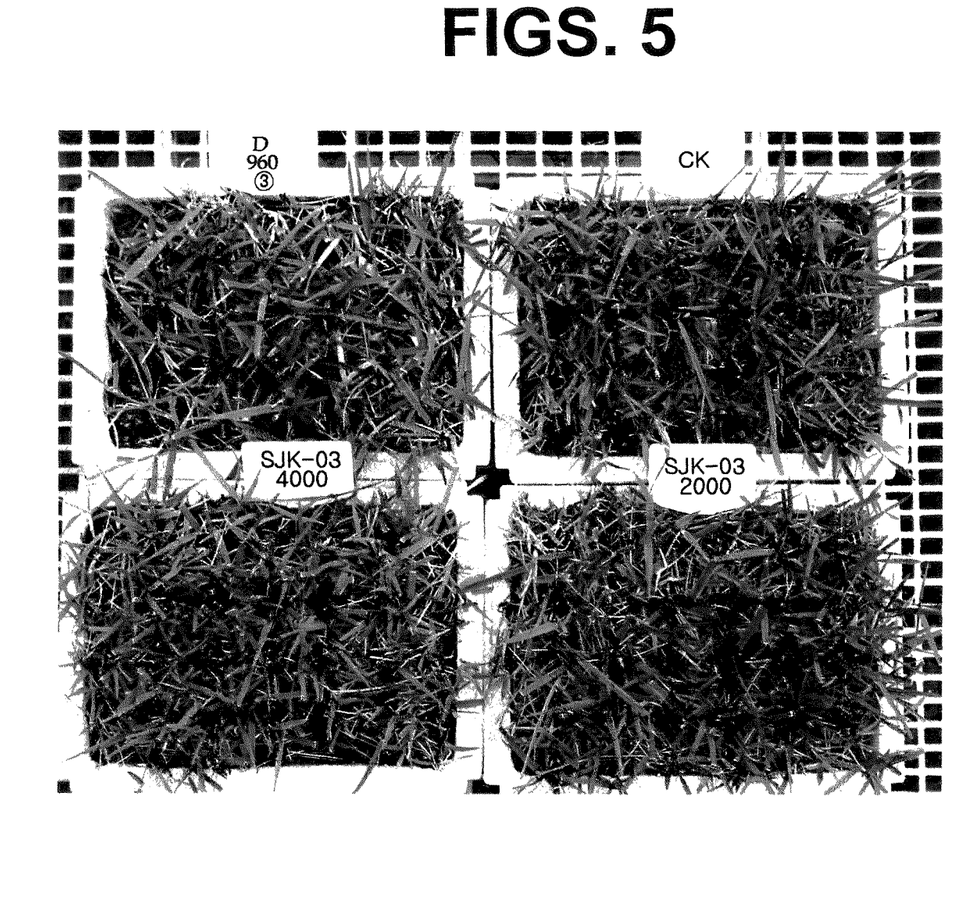
FIG. 5 shows phytotoxicity tested against zoysiagrass (*Zoysia japonica*). The photo on the left shows Dithiopyr treated zoyisagrass clearly evidencing the phytotoxicity. However, in the bottom panel wherein the test substance of the present invention was treated in a rate of 4,000 or 2,000 g/ha, no phytotoxicity was observed at all.
Figure 6:
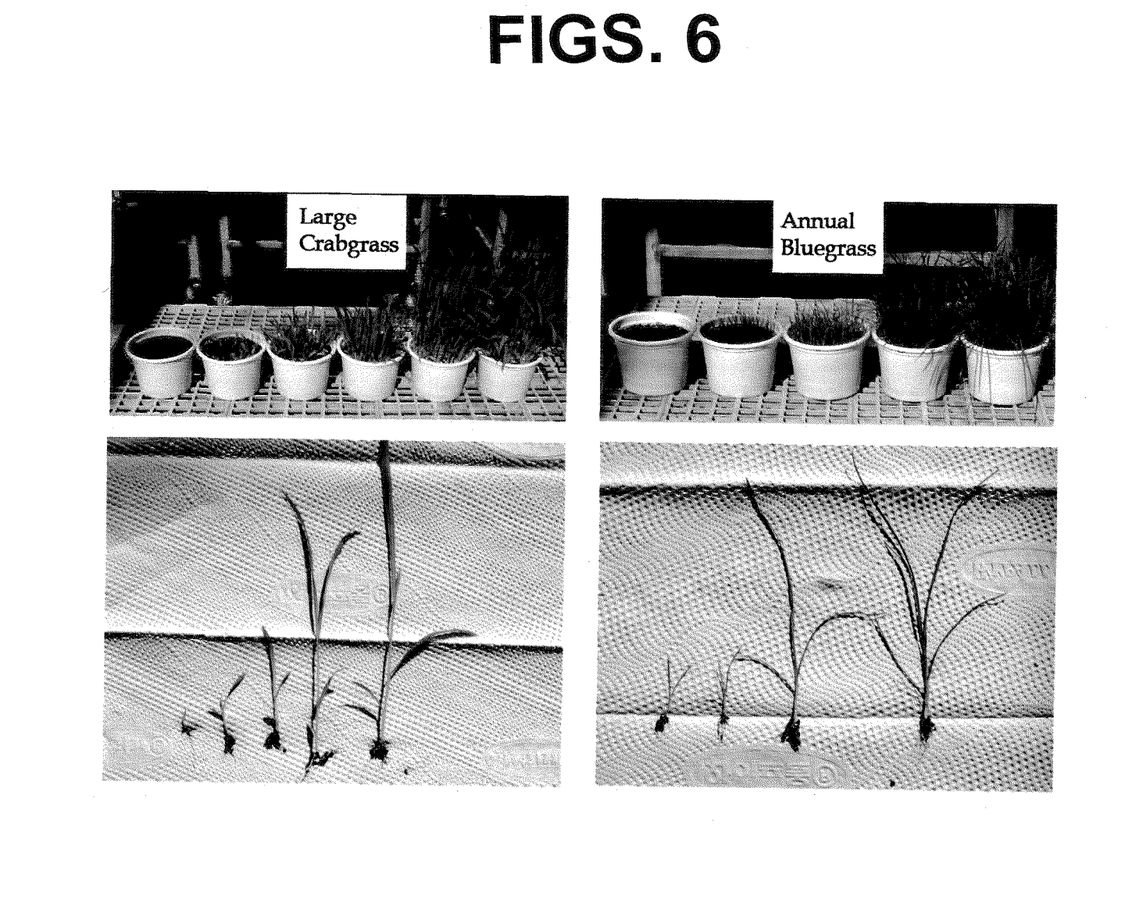
FIG. 6 shows large crabgrass and annual bluegrass at different growth stages. Large crabgrass and annual bluegrass used in the present invention include those at one- to five-leaf stages.
Figure 7:
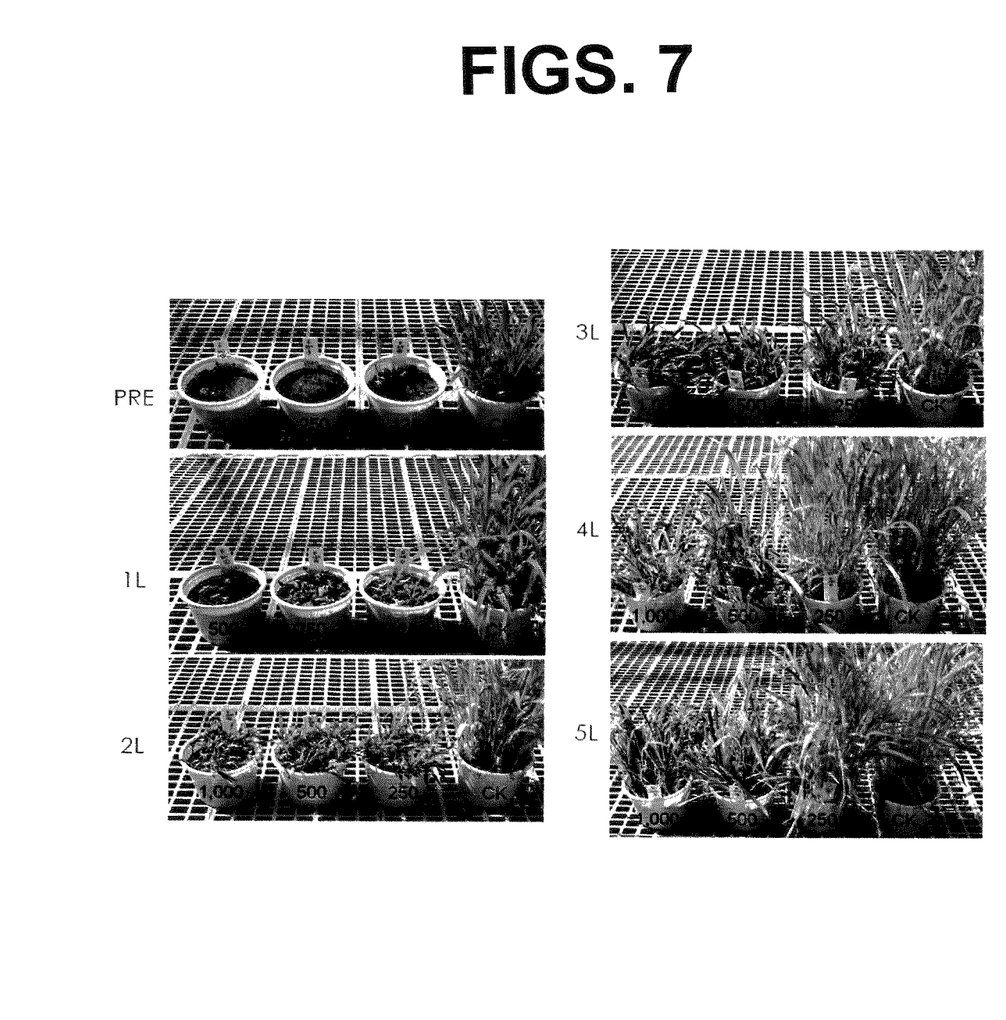
FIG. 7 shows the effect of the test substance of the present invention tested for large crabgrass. From the photo on the far left side, it represents pre-emergence (PRE) stage, and 1 leaf stage (1L) to 5-leaf stage (5L). CK indicates untreated control.
Figure 8:
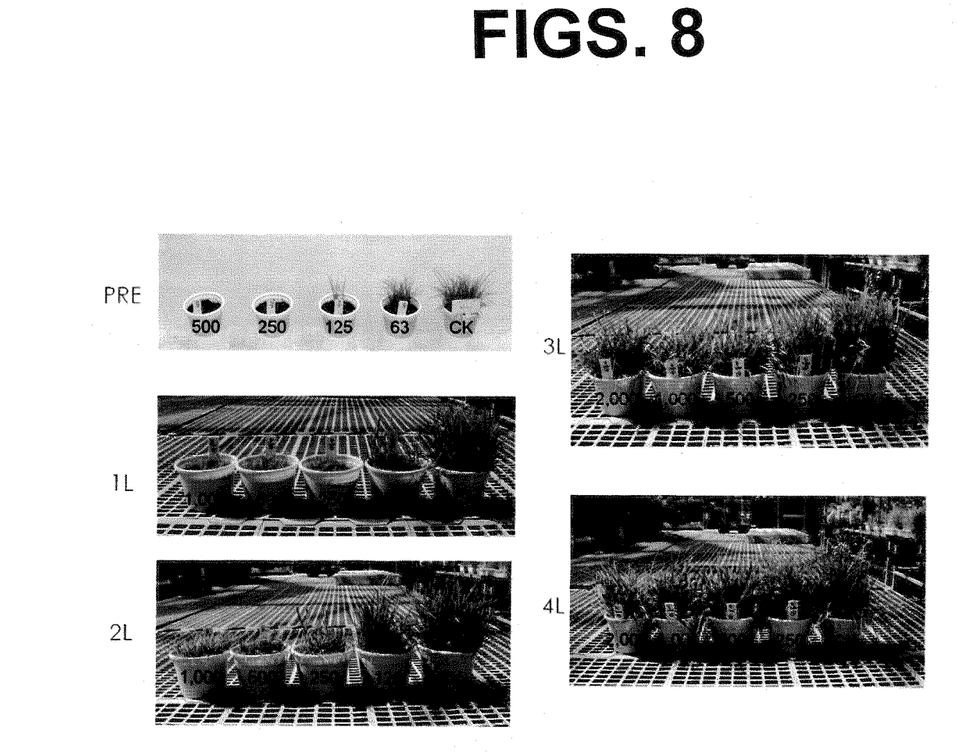
FIG. 8 shows the effect of the test substance of the present invention for annual bluegrass.

According to the above-described results of Table 2, it was found that the test substance of the present invention had an excellent safety to all types of the turfgrasses even at very high dosage of 4 kg/ha, and there was almost no phytotoxic effect when the dosage was the same or less than 0.5 kg/ha (see, FIG. 4 and FIG. 5). Compared to the reference herbicide Dithiopyr at the recommended rate (0.48 kg/ha), negligible phytotoxicity was observed with the test substance of the present invention even at 1~2 kg/ha. Thus, it is evident that the test substance of the present invention is far safer than Dithiopyr which has been widely used as a turf grass herbicide (see, FIG. 3). In addition, since the test substance of the present invention controls large crabgrass almost completely by pre-emergence application at a dosage as low as 0.06~0.12 kg/ha (see, the results of Table 1), it can be used in a wide dose range between 0.06 and 2 kg/ha for turf.

Example 3

Measurement of Herbicidal Activity for Large Crabgrass and Annual Bluegrass at Different Growth Stages The most common problematic gramineous weed in turf includes annual bluegrass in addition to large crabgrass. While large crabgrass is an annual grass which usually emerges during spring season, annual bluegrass is a biennial weed which germinates during fall season or sometimes during winter and spring season when temperature is cool. According to the result of Table 1, although the efficacy is lower in post-emergence treatment compared to pre-emergence treatment, the test substance of the present invention showed an herbicidal activity to growing weeds at higher rates. Thus, in this experiment, efficacy was more carefully evaluated in different application timing for large crabgrass and annual grass.

To a cup pot having a surface area of 100 cm$^2$ wherein mixed soils including blend bed soil (Boonong, Horticultural Bed Soil No. 3) and sandy loam soil were filled (mixing ratio, 1:1), seeds of large crabgrass and annual bluegrass were sown consecutively at an one week interval. The pots were moistened by sub-irrigation, and kept in a greenhouse maintained at 25~30° C. (day) or 15~25° C. (night). The said weeds were grown to various growth stages from pre-emergence to the four-leaf stage. Then, they were applied with the test substance of the present invention at dosage of 2, 1, 0.5, or 0.25 kg/ha. As a reference herbicide, Dithiopyr (32% EC, manufactured by Dongbu Hannong Chemical Company), was applied at 0.96, 0.48, or 0.24 kg/ha. Spray volume was adjusted to 2,000 L/ha. The method to spray of the test substance and prepare spray solutions were the same as described above. The reference herbicide was used after it was diluted with 0.2% (v/v) Tween 20 aqueous solution. The test was conducted in a randomized block design with three replicates. Two weeks after the treatment, plant parts remained above the pot soil surface were cut and the fresh weight was weighed. Results are given by a suppression ratio relative to the biomass that was obtained from the untreated group (see, Table 3).

TABLE 3

Herbicidal effect of the test substance to large crabgrass and annual bluegrass at different growth stages*

| | | Large crabgrass | | | | | Annual bluegrass | | | | |
| Herbicide | Dosage (kg/ha) | PRE | 1 leaf | 2 leaf | 3 leaf | 4 leaf | PRE | 1 leaf | 2 leaf | 3 leaf | 4 leaf |
|---|---|---|---|---|---|---|---|---|---|---|---|
| Test substance | 2 | 100 | 100 | 98 | 97 | 76 | 100 | 99 | 95 | 69 | 60 |
| | 1 | 100 | 100 | 98 | 94 | 70 | 100 | 97 | 93 | 66 | 55 |
| | .5 | 100 | 100 | 93 | 86 | 65 | 100 | 96 | 90 | 61 | 37 |
| | .25 | 100 | 100 | 81 | 72 | 33 | 100 | 95 | 82 | 18 | 2 |
| | .12 | 84 | 95 | 45 | 23 | 16 | 95 | 37 | 35 | 0 | 0 |
| Dithiopyr | .96 | 100 | 100 | 98 | 89 | 66 | 100 | 97 | 91 | 61 | 35 |
| | .48 | 100 | 100 | 95 | 89 | 57 | 100 | 95 | 88 | 44 | 10 |
| | .24 | 100 | 100 | 89 | 86 | 56 | 100 | 90 | 87 | 46 | 4 |

*suppression ratio relative to the biomass obtained from the untreated group (%)

The test substance of the present invention suppressed both large crabgrass and annual bluegrass from PRE (pre-emergence) to 2-leaf stage by ≧90% at 0.5 kg/ha or above. Large crabgrass over four-leaf stage and annual bluegrass over three-leaf stage were suppressed but were not completely controlled. When the test substance was used at a dosage of ≧1 kg/ha or more for large crabgrass at 3-leaf stage, 90% or more were suppressed. Similar tendency was found for Dithiopyr.

Taken together, the results of Table 2 and Table 3, it is confirmed that the test substance of the present invention has high safety for cold and warm season turfgrass at a dosage as high as 4 kg/ha, while can effectively control major gramineous weeds such as large crabgrass and annual bluegrass during a period from pre-emergent (PRE) to two-leaf stage at a dosage of 0.5 kg/ha and above.

Example 3-1

Selective Control of Grassy Weeds in Turf by 5-(2,6-difluorobenzyl)oxymethyl-5-methyl-3-(4-methylthiophen-5-yl)-1,2-isoxazoline (Herein after Referred to as "Test Substance")

Commercially available sod mats of zoysiagrass and bentgrass, Kentucky bluegrass, and perennial ryegrass were purchased. After cutting each turf sod mat in a size of 10 cm×20 cm, it was transplanted to a rectangular plastic pot having a surface area of 300 cm² wherein mixed soils including blend of a bed soil (Boonong, Horticultural Nursery Soil No. 3) and sandy loam soil were filled (mixing ratio, 1:1). After transplanting, the grass was mowed (0.5~1.0 cm in height) once a week, and kept for one month in a greenhouse maintained at 25~30° C. (day) or 15~25° C. (night). Then three strips of 1 cm width were removed by excision with a scissor. The open space was filled with a new soil, and seeds of large crabgrass, annual bluegrass, or goosegrass were sown. The pots were kept in a greenhouse. When the said weeds were grown up to the 3 leaf stage, another set was prepared in the same method. The first set represented post-emergence (POST) and the second set represented pre-emergence (PRE) stages of the weeds (large crabgrass, annual bluegrass, goosegrass). Then the test compound was applied at 0.25, 0.5. 1.0, 2.0, and 4.0 kg/ha. Spray was made by a track sprayer equipped with a Teejet 8002 nozzle. Spray volume was adjusted to 2,000 L/ha. The spray solution was prepared by dissolving the "test substance" in acetone and adding the same volume of 0.2% (v/v) Tween 20 aqueous solution. Four weeks after the spray of the test substance, phytotoxicity to the turfgrass and herbicidal activity to the said weeds were visually evaluated based on 0 to 100 scale (0: no phytotoxic effect, 100: completely killed). The test was conducted in a completely randomized design with 3 replicates.

The test compound did not show any visible injury at 2 kg/ha or below, and showed only minimal to acceptable injury (10~21%) to the turfgrasses even at the highest rate (4 kg/ha) tested. At the same time, the test compound controlled all the tested gramineous weeds very effectively at both PRE and POST timings in the entire dose range of 0.25 kg/ha to 4 kg/ha. This shows that the test compound selectively controls large crabgrass, annual bluegrass, and goosegrass at 0.5 to 2 kg/ha without harming the turfgrasses.

This shows that the test compound is an excellent selective herbicide. The desired plant was substantially unharmed. In the specification and the claims, "the desired vegetation is substantially unharmed" means that the desired vegetation is at most about 21% of the desired vegetation is harmed.

EFFECT OF THE INVENTION

As demonstrated by the above examples, the present invention confirms that the derivatives having general formula (I) as disclosed in Korean Patent Registration No. 392072 and 5-(2,6-difluorobenzyl)oxymethyl-5-methyl-3-(4-methylthiophen-5-yl)-1,2-isoxazoline compound, and the representative example compound as described by the formula (II), which had been disclosed as a useful paddy herbicide, have a high safety to upland crops, turfgrasses, and can control various grass weeds. As such, the said compounds can be used as an upland crop herbicide as well as a turf herbicide with high safety and an excellent herbicidal activity.

What is claimed is:

1. A method of selectively controlling annual bluegrass or goosegrass in the presence of turf grass, the method comprising:

obtaining 5-benzyloxymethyl-1,2-isoxazoline derivative compounds of the following formula (I) as an active ingredient:

(I)

wherein, $X_1$, $X_2$ and $X_3$ are each a hydrogen, a methyl group, a halogen group, a methoxy group or a nitro

TABLE 4

Selective control of large crabgrass and annual bluegrass in various turfgrasses.

| Dosage (kg/ha) | Turfgrass | | | | Weeds | | | | | |
| --- | --- | --- | --- | --- | --- | --- | --- | --- | --- | --- |
| | ZSG | BTG | KBG | PRG | LCG (PRE) | LCG (POST) | ABG (PRE) | ABG (POST) | GSG (PRE) | GSG (POST) |
| 4 | 12 | 10 | 21 | 0 | 100 | 100 | 100 | 95 | 100 | 100 |
| 2 | 0 | 0 | 0 | 0 | 100 | 100 | 100 | 92 | 100 | 100 |
| 1 | 0 | 0 | 0 | 0 | 100 | 95 | 100 | 83 | 100 | 100 |
| 0.5 | 0 | 0 | 0 | 0 | 100 | 90 | 100 | 75 | 100 | 95 |
| 0.25 | 0 | 0 | 0 | 0 | 100 | 80 | 100 | 60 | 100 | 85 |

Species: ZSG, Zoysiagrass; BTG, Bentgrass; KBG, Kentucky bluegrass; PRG, Perennial ryegrass; LCG, Large crabgrass; ABG, Annual bluegrass; GSG, Goosegrass.

group, provided that all of $X_1$, $X_2$ and $X_3$ cannot be a hydrogen at the same time; and $Y_1$, $Y_2$ and $Y_3$ are each a hydrogen or a fluorine; and applying said derivative compounds, pre-emergence or post-emergence, to the annual bluegrass or goosegrass in the presence of turf grass.

2. The method according to claim 1, wherein the said 5-benzyloxymethyl-1,2-isoxazoline derivative compound is 5-(2,6-difluorobenzyl)oxymethyl-5-methyl-3-(4-methylthiophen-5-yl)-1,2-is-oxazoline compound of the following formula (II):

(II)

3. The method according to claim 1, wherein the turf grass comprises zoysiagrass.

4. The method according to claim 1, wherein the turf grass comprises bentgrass.

5. The method according to claim 1, wherein the turf grass comprises Kentucky bluegrass.

6. The method according to claim 1, wherein the turf grass comprises perennial ryegrass.

7. The method according to claim 1, wherein said derivative compounds are applied as pre-emergence treatment.

8. The method according to claim 1, wherein said derivative compounds are applied as post-emergence treatment.

9. The method according to claim 1, wherein the compound of the formula (I) is comprised, as a single active ingredient, of 1 to 80% by weight in a final formulated product.

10. The method according to claim 1, wherein the compound of the formula (I) is comprised of 1 to 40% by weight in a final formulated product.

11. The method according to claim 1, wherein said derivative compounds are applied before a three-leaf stage of said annual bluegrass or goosegrass.

12. The method according to claim 1, wherein the annual bluegrass exists in the presence of the turf grass, and said derivative compounds are applied to the annual bluegrass in the turf grass.

13. The method according to claim 1, wherein the goosegrass exists in the presence of the turf grass, and said derivative compounds are applied to the goosegrass in the turf grass.

14. The method according to claim 1, wherein the turf grass is selected from the group consisting of zoysiagrass, bentgrass, Kentucky bluegrass, perennial ryegrass and a combination thereof.

15. The method according to claim 1, wherein the turf grass is selected from the group consisting of bentgrass, Kentucky bluegrass, perennial ryegrass, and a combination thereof; and the annual bluegrass exists in the presence of the turf grass, and said derivative compounds are applied to the annual bluegrass in the presence of the turf grass.

16. A method of selectively controlling annual bluegrass in turf grass selected from the group consisting of bentgrass, Kentucky bluegrass, perennial ryegrass, and a combination thereof while leaving the turf grass substantially unharmed, the method comprising:

obtaining 5-benzyloxymethyl-1,2-isoxazoline derivative compounds of the following formula (I) as an active ingredient:

(I)

wherein, $X_1$, $X_2$ and $X_3$ are each a hydrogen, a methyl group, a halogen group, a methoxy group or a nitro group, provided that all of $X_1$, $X_2$ and $X_3$ cannot be a hydrogen at the same time; and $Y_1$, $Y_2$ and $Y_3$ are each a hydrogen or a fluorine; and applying said derivative compounds, pre-emergence or post-emergence, to the annual bluegrass in the presence of turf grass.

17. The method according to claim 16, wherein the said 5-benzyloxymethyl-1,2-isoxazoline derivative compound is 5-(2,6-difluorobenzyl)oxymethyl-5-methyl-3-(4-methylthiophen-5-yl)-1,2-isoxazoline compound of the following formula (II):

(II)

18. The method according to claim 16, wherein the compound of the formula (I) is comprised, as a single active ingredient, of 1 to 80% by weight in a final formulated product.

19. The method according to claim 16, wherein the compound of the formula (I) is comprised of 1 to 40% by weight in a final formulated product.

20. The method according to claim 16, wherein a dosage of said derivative compounds is in the range of 0.5 to 2-4 kg/ha.

* * * * *